United States Patent
Nakamura

(10) Patent No.: US 8,466,418 B2
(45) Date of Patent: Jun. 18, 2013

(54) GAMMA RAY DETECTOR, RADIATION DIAGNOSTIC DEVICE, TOMOGRAPHY DEVICE, AND METHOD OF ANALYZING TOMOGRAPHY DEVICE

(75) Inventor: Hidehito Nakamura, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 201 days.

(21) Appl. No.: 12/999,212

(22) PCT Filed: Jun. 25, 2009

(86) PCT No.: PCT/JP2009/061662
§ 371 (c)(1),
(2), (4) Date: Dec. 15, 2010

(87) PCT Pub. No.: WO2009/157526
PCT Pub. Date: Dec. 30, 2009

(65) Prior Publication Data
US 2011/0127435 A1 Jun. 2, 2011

(30) Foreign Application Priority Data
Jun. 25, 2008 (WO) .................. PCT/JP2008/061586

(51) Int. Cl.
*G01T 1/164* (2006.01)
*G01T 1/166* (2006.01)

(52) U.S. Cl.
USPC ................................. 250/363.03; 250/363.04

(58) Field of Classification Search
USPC .................. 250/368, 363.02, 363.03, 363.04
See application file for complete search history.

(56) References Cited

U.S. PATENT DOCUMENTS

2006/0202125 A1 9/2006 Suhami
2009/0159804 A1 6/2009 Shibuya et al.

FOREIGN PATENT DOCUMENTS

| JP | A-5-66275 | 3/1993 |
|---|---|---|
| JP | A-7-311270 | 11/1995 |
| JP | A-09-230052 | 9/1997 |
| JP | A-2001-159682 | 6/2001 |
| JP | A-2004-093383 | 3/2004 |
| JP | A-2005-017142 | 1/2005 |
| JP | A-2007-71858 | 3/2007 |
| JP | A-2008-45948 | 2/2008 |
| JP | A-2008-51701 | 3/2008 |
| WO | WO 2008/035708 A1 | 3/2008 |

OTHER PUBLICATIONS

Suzuki et al., "Performance of Prototype Hard X-ray Polarimeter Utilizing Compton Scattering," Japanese Journal of Applied Physics, 2006, pp. 274-278, vol. 45-No. 1A.
International Search Report mailed Oct. 6, 2009 issued in International Patent Application No. PCT/JP2009/061662 (with translation).

*Primary Examiner* — David Porta
*Assistant Examiner* — Faye Boosalis
(74) *Attorney, Agent, or Firm* — Oliff & Berridge, PLC

(57) ABSTRACT

A gamma ray detector for detecting a gamma ray emitted from a target of measurement includes: an organic scintillator for detecting Compton electrons resulting from a gamma ray emitted from the target of measurement; an inorganic scintillator for detecting a Compton gamma ray; and photodetector modules for detecting light generation in the corresponding scintillators. Light generation signals from the organic and inorganic scintillators are synchronously measured, and a detection window of a gamma ray is generated. Thus, an inexpensive radiation diagnostic device of an ultra-high S/N ratio and low cost is provided.

29 Claims, 17 Drawing Sheets

(A) Determination of synchronous measurement (B) If there is overlap (C) If there is no overlap (B) Solid angle from light source (A) Light propagation (A) Two-dimensional coordinates (B) Three-dimensional coordinates ✧ Interaction point
⟶ Gamma ray
⤑ Compton scattered gamma ray
⤏ Compton scattered electron

Fig. 22

| | Clock | Organic flag | Inorganic flag | Result |
|---|---|---|---|---|
| | . | | | |
| | . | | | |
| | . | | | |
| | . | | | |
| | 10001 | | | |
| Synchronous scanning window 10002 | 10002 | 45 | | TRUE |
| | 10003 | | 55 | |
| | 10004 | | | |
| | 10005 | | | |
| 10006 | 10006 | 30 | 70 | TRUE |
| | 10007 | | | |
| | 10008 | | | |
| | 10009 | | | |
| 10010 | 10010 | 50 | | TRUE |
| 10011 | 10011 | 50 | 50 | TRUE |
| | 10012 | | | |
| | 10013 | | | |
| 10014 | 10014 | 50 | | FALSE |
| | 10015 | | 50 | |
| | 10016 | | 50 | |
| | 10017 | | | |
| Synchronous scanning window 10018 | 10018 | 40 | 60 | FALSE |
| | 10019 | | 10 | |
| | 10020 | | | |
| | . | | | |
| | . | | | |
| | . | | | |

GAMMA RAY DETECTOR, RADIATION DIAGNOSTIC DEVICE, TOMOGRAPHY DEVICE, AND METHOD OF ANALYZING TOMOGRAPHY DEVICE

TECHNICAL FIELD

The present invention relates to a gamma ray detector, a radiation diagnostic device, a tomography device, and a method of analyzing the tomography device. In particular, the invention relates to a super high sensitive gamma ray detector that can be realized at low cost without using a collimator, a radiation diagnostic device using the gamma ray detector, a tomography device, and a method of analyzing the tomography device.

BACKGROUND ART

Positron emission tomography (PET) using a labeling agent exhibiting excellence in sensitivity and quantitative performance has widely been used in clinical practice in recent years in order to obtain information that can be reflected in a treatment plan such as cancer detection, determination of benignity versus malignancy, determination of the effect of treatment, diagnosis of relapse, and prognostic prediction. Widespread use of PET testing develops a fear of exposure of examinees and healthcare workers (doctors, radiographers and nurses) to radiation. Controlling the exposure to a minimum possible level is an important problem to be solved. Meanwhile, in order to ease examinee's anxiety during testing, it is desired that a radiation diagnostic device with high resolution and high detection efficiency capable of making a determination promptly and appropriately be offered at low cost.

An example of a gamma ray detector used in such a radiation diagnostic device is disclosed in Patent Document 1. In the gamma ray detector disclosed therein, a collimator, NaI (sodium iodide), and a PMT (photomultiplier tube) are stacked. Parallel holes of a small diameter are defined in the lead collimator, and only those gamma rays that travel from a direction of the holes are guided by the collimator to a single crystal of NaI. Then, fluorescent light of an intensity proportionate to the energy transfer from the gamma rays is generated at the single crystal. The fluorescent light is detected by the PMT, so that the intensity and position of the gamma rays are determined.

Patent Document 2 discloses a dual-purpose device functioning both for SPECT (single photon emission computed tomography) and PET where gamma ray detectors are arranged to place a target of measurement therebetween.

Further, Patent Document 3 discloses a gamma ray detector where a group of scintillators with a large number of columnar scintillators closely connected together, and an APD array with a large number of avalanche photodiodes (APD) closely connected to the scintillators, are optically coupled.

[Patent Document 1] Japanese Patent Application Laid-Open No. Hei. 5-66275
[Patent Document 2] Japanese Patent Application Laid-Open No. 2001-159682
[Patent Document 3] Japanese Patent Application Laid-Open No. Hei. 7-311270

However, there are problems that use of a collimator as in the technique disclosed in Patent Document 1 increases the weight and size of a detector. The technique disclosed in Patent Document 2 finds it difficult to accurately specify the position of a radionuclide. Further, the technique disclosed in Patent Document 3 requires a radiation detector of a complicated structure.

DISCLOSURE OF INVENTION

The present invention has been made to solve the foregoing problems of the conventional techniques. An object of the invention is to provide a gamma ray detector at low cost that is capable of realizing an ultra-high S/N ratio, high-energy resolution, high spatial resolution, and high temporal resolution.

The invention solves the foregoing problems in the way as follows. A gamma ray detector for detecting a gamma ray emitted from a target of measurement includes: an organic scintillator for detecting Compton electrons resulting from a gamma ray emitted from the target of measurement; an inorganic scintillator for detecting a Compton gamma ray; and photodetectors for detecting light generation in the corresponding scintillators. The gamma ray detector performs synchronous measurement to select a pair according to the same event by using a detected time and detected energy detected by each of the photodetectors on the basis of light generation in the organic scintillator and the inorganic scintillator.

If the detector modules are provided as a pair, the detector modules each perform synchronous measurement, thereby enhancing performance of noise removal.

A detection window of a gamma ray when a determination of synchronous measurement may be made as a standard of a detected time of light generation in the organic scintillator.

The interval of a detection window to be generated may be changed between when a very short short-time window appropriate to the time width of light generation in the organic scintillator and a relatively long long-time window appropriate to the time width of light generation in the inorganic scintillator overlap each other, and when they do not overlap each other. This enhances measurement accuracy.

If the very short short-time window appropriate to the time width of light generation in the organic scintillator and the relatively long long-time window appropriate to the time width of light generation in the inorganic scintillator overlap each other, an overlapping interval may be defined as a detection window, and may be employed as a standard of a detected time.

If the very short short-time window appropriate to the time width of light generation in the organic scintillator and the relatively long long-time window appropriate to the time width of light generation in the inorganic scintillator do not overlap each other, the very short short-time window appropriate to the time width of light generation in the organic scintillator may be defined as a detection window, and may be employed as a standard of a detected time.

A detected time and detected energy detected by the photodetector for the inorganic scintillator, and those detected by the photodetector for the organic scintillator may be scanned along the time axis within a synchronous scanning window of a predetermined time width. Then, a flag in the synchronous scanning window can be detected immediately before the synchronous scanning window passes through an organic flag.

Further, a sum of detected energy of all flags in the synchronous scanning window may be obtained immediately before the synchronous scanning window passes through the organic flag. If the sum is smaller than a reference level of emitted energy of a gamma ray, the organic flag may be determined as a noise.

The energy of the organic flag may be detected immediately before the synchronous scanning window passes through the organic flag. If the detected energy is greater than a reference level of emitted energy of a gamma ray, the organic flag may be determined as a noise.

Further, the accuracy of a time measured in simultaneous measurement may be enhanced by measuring the time on the basis of the synchronous measuring window.

Gamma rays emitted from the target of measurement can be reconstructed by adding the absorbed amounts of energy of the gamma rays synchronously measured in the two types of scintillators.

A region of emission from the target of measurement can be limited by arranging the detector modules as a pair to place the target of measurement therebetween, and by making each of the detector modules reconstruct a gamma ray.

A position of emission from the target of measurement can be specified to that on a line without performing Fourier conversion by arranging the detector modules as a pair to place the target of measurement therebetween, and by connecting positions by the line where gamma rays are generated in the corresponding organic scintillators.

The above-described limited region of emission can be specified to a line in the foregoing way.

A distance from the organic scintillator to the target of measurement may be determined in the above-described limited region of emission by analyzing a time of flight.

The time of flight can be analyzed by using the respective outputs from the foregoing detector modules as a pair.

The inorganic scintillator may be arranged on a side surface of the organic scintillator.

The inorganic scintillator may have a wedge shape with a sharp edge pointing to the target of measurement.

The photodetector can be arranged such that a photo-detecting section of the photodetector optically faces part of a light extraction surface of the scintillator. A photodetector for obtaining a distribution of light generation in the X direction based on a fluorescence distribution analysis technique, and a photodetector for obtaining a distribution of light generation in the Y direction based on the fluorescence distribution analyzing technique, may be provided on the optically facing part.

The photodetectors can be arranged along the X and Y central axes of the light extraction surface of the scintillator.

Data obtained by simultaneous measurement of a synchronously measured event may be constructed into an image without performing Fourier conversion. This reduces time for image formation while enhancing image accuracy.

The gamma ray detector may be employed as a single detector module.

The gamma ray detector may be employed as a detector for an SPECT device.

The gamma ray detector may be employed as a detector for a PET device.

The invention is also intended to provide a radiation diagnostic device where the gamma ray detector is arranged around a target of measurement.

The invention is also intended to provide a tomography device where the gamma ray detectors are arranged as a pair in order to detect annihilation gamma rays as a pair emitted in opposite directions from a target of measurement.

The invention is also intended to provide a tomography device for analyzing times of flight by using outputs from the gamma ray detectors as a pair.

The invention is also intended to provide a method of analyzing a tomography device. The method is performed on the foregoing tomography device, and includes: a step of identifying energy in a detection window of a gamma ray suitable for characteristics of the organic scintillator; a step of identifying a gamma ray by using a sum of energy of the organic scintillator and the inorganic scintillator; a step of calculating fluorescent coordinates in the organic scintillator by using a scintillation distribution within the organic scintillator; a step of specifying a region specified only by energy information to a line by connecting fluorescent coordinates in the two organic scintillators as a pair by a line; and a step of specifying three-dimensional coordinates of a radionuclide on the line by using a difference between arrival times of gamma rays at the two organic scintillators as a pair.

The invention is also intended to provide a computer program readable from a recording medium, and which causes a computer to execute the method of analyzing a topography device.

The invention is also intended to provide a computer-readable recording medium where the computer program is stored.

An organic scintillator has conventionally been considered as inappropriate for gamma ray detection due to its low density that causes a plenty of gamma rays to pass therethrough. Meanwhile, in the invention, an organic scintillator is combined with an inorganic scintillator, and a synchronous measuring technique that is a newly developed analysis method is employed. Thus, the invention makes it possible to detect a gamma ray in a wide-energy region (ranging from several tens of kilo-electron volts to some mega-electron volts). Next, the characteristics of the invention in terms of software, and those of the invention in terms of hardware are described in this order.

The characteristics of the invention in terms of software include a synchronous measuring technique. In the synchronous measuring technique, a pair based on the same event is selected according to detected time and detected energy detected by each of photodetectors for detecting light generation in organic and inorganic scintillators. The synchronous measuring technique is described next by referring to the flow charts of FIGS. 20 and 21.

As shown in FIG. 20, a detector module of the invention includes an organic light generation signal (Sa1-1) and an inorganic light generation signal (Sa1-2) for detecting gamma rays, and processing circuits A1 (Sa2-1) and A2 (Sa2-2) for photoelectrically converting the corresponding light generation signals. Each processing circuit generates an electric signal containing information about the time and energy (T/E) of a detected gamma ray on the basis of the corresponding light generation signal.

In the synchronous measuring technique shown in FIG. 20, electric signals generated by the processing circuits A1 and A2 are processed by sequentially following a series of statuses including creation of a T/E memory (Sa3), synchronous window scanning (Sa4), E check (S5), determination of synchronous measurement (Sa6), and creation of a pair list (Sa7). Then, a noise event is removed from a light generation signal of a gamma ray detected by the detector module, and the organic light generation signal (Sa1-1) and the inorganic light generation signal (Sa1-2) based on a true event are selected as a pair. Here, a description is given of a process content for respective statuses on the basis of the assumption that a gamma ray with energy F enters the detector module (S0).

First, in the creation of a T/E memory (Sa3), electric signals generated by the processing circuits A1 and A2 are placed in a table as shown in FIG. 22 that is to be stored in a memory. In the example shown in FIG. 22, the organic light generation signal (Sa1-1) is written into a column of organic flags, and the inorganic light generation signal (Sa1-2) is written into a column of inorganic flags in their respective rows of clock times when the organic light generation signal (Sa1-1) and the inorganic light generation signal (Sa1-2) are generated. The organic light generation signal (Sa1-1) and the inorganic light generation signal (Sa1-2) are written as energy represented by numerical values. The numerical values indicate the relative values of energy.

In the synchronous window scanning (Sa4), scanning is performed in a window of a predetermined time width δT in ascending order of the number of clocks in the T/E memory table shown in FIG. 22, thereby detecting an energy flag in the window. This scanning of temporal information is intended to check if a gamma ray scattered once in an organic scintillator is detected by an inorganic scintillator. In the scanning, attention is first focused on an organic flag to detect the organic flag at the rear end of the aforementioned time width. Then, a different flag in the window is detected. That is, scanning is performed to see if a different flag is present within the time δT after the organic flag. If such a different flag is detected, the energy value of each flag is read. Then, a status goes to the E check (Sa5) in a subsequent step.

A status in the E check (Sa5) is to check up data in order to select a pair of signals (TRUE signals) generated from the same gamma ray and on the basis of a true event from the organic light generation signal (Sa-1) and the inorganic light generation signal (Sa-2) by using energy information. Here, a sum of organic energy E-1 and inorganic energy E-2 is obtained. Then, a check is made to see if the sum falls within a range of error (±δE) of the energy (E) of the gamma ray having entered the detector module. In FIG. 22, E±δE is set to 100±3 to determine a candidate for TRUE. If the sum falls within the range of energy, a status goes to the determination of synchronous measurement (Sa6). In FIG. 22, synchronous scanning windows 10002, 10006, 10011, and 10014 become TRUE signals. A sum of energy of organic and inorganic flags exceeds 100±3 in a synchronous scanning window 10018. Thus, the synchronous scanning window 10018 is treated simply as a FALSE signal, namely as a noise. However, if the number of events of TRUE signals is small, the clock, the predetermined time δT, and the error δE of energy may be reset and analyzed again even for the FALSE signal in the synchronous scanning window 10018, thereby obtaining a TRUE signal.

A status in the determination of synchronous measurement (Sa6) is to make a determination that the organic light generation signal (Sa1-1) and the inorganic light generation signal (Sa1-2) are signals as a pair generated from the same gamma ray and on the basis of a true event. This determination is made based on information about time and energy checked up in the synchronous window scanning (Sa4) and in the E check (Sa5). After the determination is made, data of the signals as a pair is transferred to a status in the creation of a pair list (Sa7) in a subsequent step where a list of TRUE data is created.

The status in the creation of a pair list (Sa7) is to count the number of true events, and place information containing event numbers, the organic light generation signal (Sa-1), and the inorganic light generation signal (Sa-2) in a table.

After the series of statuses described above, a true event can be selected from signals measured in the organic and inorganic scintillators. A status proceeds to the synchronous window scanning (Sa4), and then the E check (Sa5) in the flow chart of FIG. 20. However, the synchronous measuring technique is also applicable if these statues are performed in reverse order.

One detector module is used in the foregoing description. If two detector modules are used, by causing each of the detector modules to perform synchronous measurement and adding statuses of simultaneous measuring window scanning (S9), determination of simultaneous measurement (S10), and creation of simultaneous measurement list (S11) as shown in FIG. 21, data can be analyzed with a high degree of accuracy by using a conventionally known simultaneous measuring technique or TOF (time-of-flight).

FIG. 23 shows how to make a determination of whether a signal is based on a true event performed in the statuses including the synchronous window scanning (Sa4), the F check (Sa5), the determination of synchronous measurement (Sa6), and the creation of a pair list (Sa7). A synchronous scanning window (window) will be described in more detail below. As described above, the synchronous scanning window is of the predetermined time width δT. Scanning is performed in the window in ascending order of the number of clocks in the table of the T/E memory (Sa3) shown in FIG. 22, thereby detecting an energy flag in the window.

When a photodetector for an inorganic scintillator and a photodetector for an organic scintillator start detection, scanning is started in the synchronous scanning window along the time axis (Sc-1). Organic detecting energy (standard organic detecting energy) is detected (Sc-3) when a flag of the organic detecting energy is detected. The detected value is compared with the energy of a gamma ray emitted from within a body (called standard energy), for example, of 511 keV (Sc-4). If the detected value is greater (Sc-5), the detected value is determined as a noise (Sc-9). If the detected value is not greater, the detected value is determined as a noise (Sc-9) on condition that there are two or more flags of organic detecting energy in the synchronous scanning window (Sc-6) immediately before the organic detecting energy passes through the synchronous scanning window. If there is one flag, total energy in the synchronous scanning window is obtained. If the total value does not fall within the range of the standard energy, the detected value is determined as a noise (Sc-7). If the total value falls within the range, the detected value is determined as a signal based on a true event (Sc-8). Then, the standard organic detecting energy and the inorganic detecting energy counted in the step (Sc-6) are written as a pair into a pair list in a subsequent status (Sc-10).

The characteristics of the invention in terms of the hardware of a detector are described next.

1. Enhancement of Detection Efficiency of Radiation Diagnostic Device by Realizing High Sensitivity (S/N)

1-1. Realization of High Sensitivity

Reducing a background to a minimum possible level is an important key to realization of high sensitivity (S/N). A main background N (counts/sec) in a medical diagnostic device includes the following two. One is an event $B_{DE}$ resulting from Compton scattering in a scintillator. The other is a simultaneous measuring event $B_{DT}$ occurring accidentally.

A background can be expressed by the following formula:

$$N = B_{DE} + b_{DT} \tag{1}$$

1-2. Reuse of Compton Scattering Event

Here, the aforementioned backgrounds are reduced as follows.

In a conventionally employed PET, a noise signal of a gamma ray resulting from Compton scattering is present in the energy region of a gamma ray to be measured.

A background event resulting from this Compton scattering can be expressed by the following formula by using the energy window DE (keV) of a detector. Here, b (counts/sec/keV) is a background number in the energy window resulting from the Compton scattering:

$$B_{DE} = DE \times b \tag{2}$$

1-3. Measurement of Gamma Ray by Using Organic and Inorganic Scintillators

In order to reduce b, a scintillator of a detector is provided in a module of the following configuration.

Organic and inorganic scintillators, and a photodetector are prepared to form a single module. A gamma ray emitted from within a target of measurement is measured in a two-way process by the organic and inorganic scintillators.

First, the organic scintillator detects Compton electrons. Next, the inorganic scintillator detects a Compton gamma ray. Energy obtained by the two scintillators is added together, and a peak of the gamma ray is established, thereby realizing detection.

The foregoing configuration makes b substantially zero. Thus, a noise resulting from the Compton scattering has substantially no influence in the energy region of the gamma ray.

1-4. Removal of Accidental Event

A photodetector module includes a scintillator, and a processor in a subsequent stage.

A background event occurring accidentally can be expressed as follows by using the detection window (time width) $\Delta T$ (sec) of the detector module. In the following, N1 (counts/sec) and N2 (counts/sec) indicate detection rates of a gamma ray by two scintillators.

$$B_{DT}=2 \times DT \times N_1 \times N_2 \qquad (3)$$

Accordingly, the characteristics of an organic scintillator are utilized. The time response of an organic scintillator is faster than the response function of an inorganic scintillator on the order of several digits (1/1000). By setting a detection window DT used for detecting a gamma ray short according to the characteristics of an organic scintillator, an accidentally occurring background event is reduced on the order of several digits, compared to conventionally used diagnostic devices.

An S/N ratio can be expressed by the following formula:

$$\eta = \frac{S}{N} = \frac{S}{2\Delta T \cdot N_1 \cdot N_2 + \Delta E \cdot b} \qquad (4)$$

Thus, a high-sensitivity S/N ratio is realized by reducing $\Delta T$ and b that constitute B.

2. Enhancement of Resolution of Radiation Diagnostic Device by Realizing High Resolution

2-1. High-Performance TOF Diagnostic Device

An organic scintillator has been used as a TOF detector in various experimental units. An inorganic scintillator of slow time response has been mainly used in the conventionally employed PET, making it difficult to put TOF PET to practical use.

In contrast, a hybrid diagnostic device of the invention with organic and inorganic scintillators makes use of fast time response that constitutes the characteristics of an organic scintillator, thereby allowing TOF PET to be put to practical use.

2-2. Realization of High-Energy Resolution

Energy resolution at the time of reconstruction of a gamma ray is always between energy resolutions of inorganic and organic scintillators. Accordingly, energy resolution $\sigma_\Sigma$ at the time of reconstruction of a gamma ray can be expressed by the following formula:

$$E_E = E_{org} + E_{Inorg} \qquad (5)$$

$$\sigma_\Sigma^2 = (E_{Org}/E_\Sigma)^2 \sigma^2_{Org} + \{(E_\Sigma - E_{org})/E_\Sigma\}^2 \sigma^2_{Inorg} \qquad (6)$$

$$\sigma_{Inorg} \leq \sigma_\Sigma \leq \sigma_{Org} \qquad (7)$$

where $E_\Sigma$ is the energy of a reconstructed gamma ray, $E_{Org}$ is energy obtained in an organic scintillator, $E_{Inorg}$ is energy obtained in an inorganic scintillator, $\sigma_{Org}$ is the energy resolution of the organic scintillator, and $\sigma_{Inorg}$ is the energy resolution of the inorganic scintillator.

As described above, by combining the two scintillators, energy resolution comparable to that of an inorganic scintillator is obtained at the time of reconstruction.

It is assumed, for example, that a plastic scintillator is used as an organic scintillator, and NaI is used as an inorganic scintillator. In this case, energy resolution of about 7.5% (FWHM) is obtained for a 662 keV gamma ray (whereas in the case of BGO used in the conventional PET, energy resolution is about 17% (FWHM)).

2-3. Realization of High Spatial Resolution

Many places of the world compete against one another for pixilation of an inorganic scintillator in order to realize high spatial resolution. However, due to high density of a constitutive substance of an inorganic scintillator, a gamma ray having entered the inorganic scintillator causes multiple scattering in the scintillator, thereby generating a large number of fluorescent light sources in the scintillator. A fluorescent light source should be evaluated correctly in order to obtain high spatial resolution. However, while a large number of fluorescent light sources are generated within a short distance (within some millimeters), a large mass number of the inorganic scintillator negatively functions to make the fluorescent light sources look as if they were a single light source. This leads to degradation of spatial resolution.

In view of this, the characteristics of an organic scintillator are utilized in the invention. As a result of low density of a constitutive substance of an organic scintillator, a gamma ray having entered the organic scintillator is very unlikely to generate multiple scattering in the scintillator. Accordingly, not many fluorescent light sources are generated in the scintillator. Further, scintillation light generated in the scintillator has a very low attenuation factor. This allows the three-dimensional coordinates of an interaction point of a gamma ray in the scintillator to be obtained accurately by using a distribution of scintillation light obtained by measurement.

3. Cost Reduction of Detector Module and its Processor

A detector is formed utilizing an organic scintillator as a basis. This allows significant cost reduction compared to a conventionally used detector module formed utilizing an inorganic scintillator as a basis.

It is assumed that a photodetector for obtaining a distribution of light generation in the direction of the X axis, and a photodetector for obtaining a distribution of light generation in the direction of the Y axis above a light extraction surface (XY plane) of a scintillator are provided on the light extraction surface, and that these photodetectors are arranged to optically face the light extraction surface. In this case, a position at which fluorescent light is generated in a scintillator can be detected on the basis of a fluorescence distribution analysis technique of the invention. This takes advantage of the fact that, while light is not generated at a position immediately above a detector, conical projection of generated light onto the light extraction surface of the scintillator allows a detector (not optically facing detector) to detect the light, even if the detector does not exist at a position directly below the position of the generated light. This eliminates the need to provide photo-detecting elements of photodetectors to cover the light extraction surface of the scintillator in its entirety, in such a manner that the photo-detecting elements uniformly and optically face the light extraction surface. Thus, a number of detecting elements can be reduced, leading to cost reduction of a photodetector and speed-up in processing detected data.

4. Compact Diagnostic Device

Medical diagnostic devices can be developed in a short period of time by modularizing a detector. A detector module can be treated as an independent detector, so that evaluation of the performance of an individual detector module is utilized in a diagnostic device of a final form. This facilitates energy calibration and the like of the diagnostic device.

An inorganic scintillator may be provided on a side surface of an organic scintillator. Scintillation from each scintillator is collected by a photodetector provided on a light extraction surface of the scintillator.

Use of an inexpensive, and easy-to-process organic scintillator allows early practical application of medical diagnostic devices and large-scale manufacturing thereof. Further, incorporating an organic scintillator into a device achieves sensitivity to alpha rays and beta rays as well as to gamma rays (X rays). This allows determination of a position of a substrate deposited on skin or cloth, identification of emitted radiation particles, measurement of a dosage thereof, and measurement of collapse time when a radiation incident occurs to cause emergency exposure. These performances reduce a time for measuring a radiation ray emitted from a body. In addition, mental burden of an examinee is minimized while prompt and adequate diagnosis of the examinee is provided.

Establishment of a detector by using a hybrid scintillator not only realizes a technical breakthrough of the detection efficiency, energy resolution, spatial resolution, and temporal resolution of a radiation ray, but also provides universality as basic principles of radiation measurement in various fields including radiation physics, medical physics, and global environment physics.

Modularizing a detector makes it possible to change the number of modules or the size of a module depending on its intended use, thereby allowing application to various types of radiation detectors. Further, applying organic and inorganic scintillators for use as a scintillator of a detector module allows detection of alpha rays, beta rays and gamma rays (X rays). The detector realizes high performance without requiring a collimator. Thus, the foregoing single detector module can be used as a portable radiation detector.

BRIEF DESCRIPTION OF DRAWINGS

FIG. 22 is a data table used in the synchronous measuring technique.

BEST MODES FOR CARRYING OUT INVENTION

Embodiments of the invention are described in detail with reference to drawings.

Figure 1:
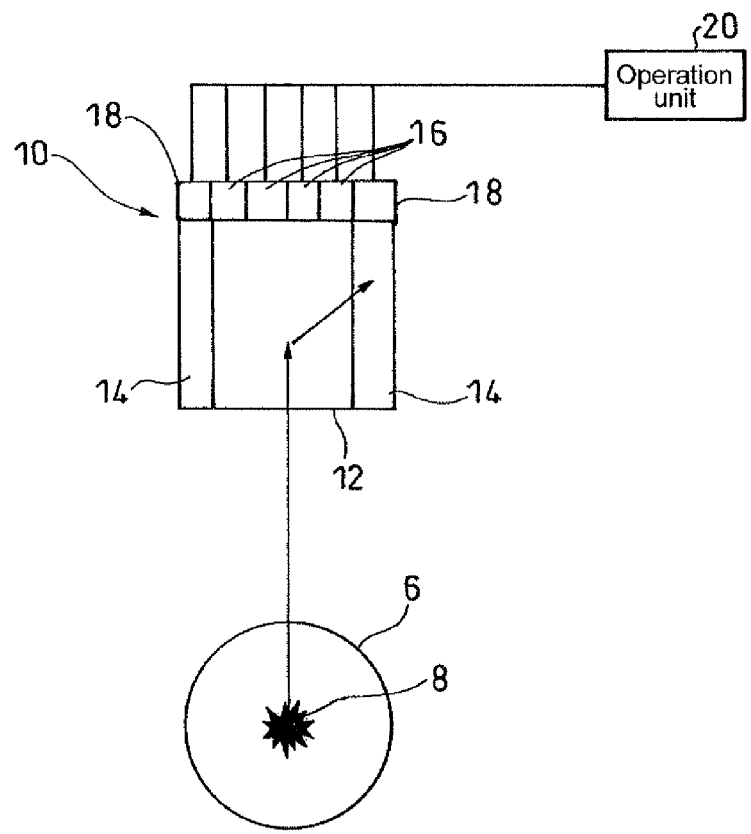
FIG. 1 is a sectional view showing a first embodiment of a detector module according to the present invention.

As shown in FIG. 1, a detector module 10 of a first embodiment of a gamma ray detector according to the present invention includes: an organic scintillator 12 for detecting Compton electrons resulting from a gamma ray emitted from a radionuclide 8 in a target of measurement 6; inorganic scintillators 14 for detecting a Compton gamma ray; photodetectors 16 and 18 such as PMTs and semiconductor detectors, for detecting light generation in the scintillators 12 and 14; and an operation unit 20. The operation unit 20 adds the absorbed amounts of energy of gamma rays synchronously measured in the two types of scintillators 12 and 14 to reconstruct gamma rays emitted from the target of measurement 6. The operation unit 20 also determines an arrival time by using Compton electrons absorbed in the organic scintillator 12.

The size of the detector module 10 can be changed to conform to the energy of a radiation ray to be measured.

Examples of the organic scintillator 12 include a plastic scintillators and p-terphenyl.

Examples of the inorganic scintillators 14 include BGO, GSO, NaI (T1), GaF2 (EU), CsI (TI), CsI (pure), and BaF2.

Figure 2:
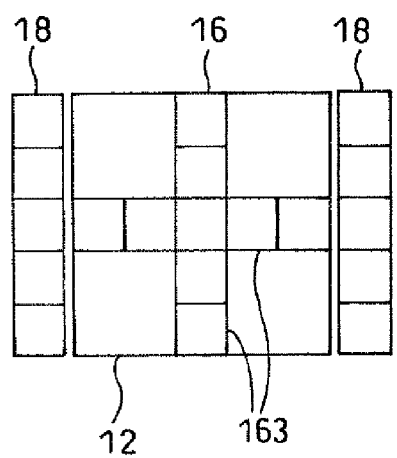
FIG. 2 is a plan view illustrating an exemplary arrangement of photodetectors in the detector module.
Figure 3:
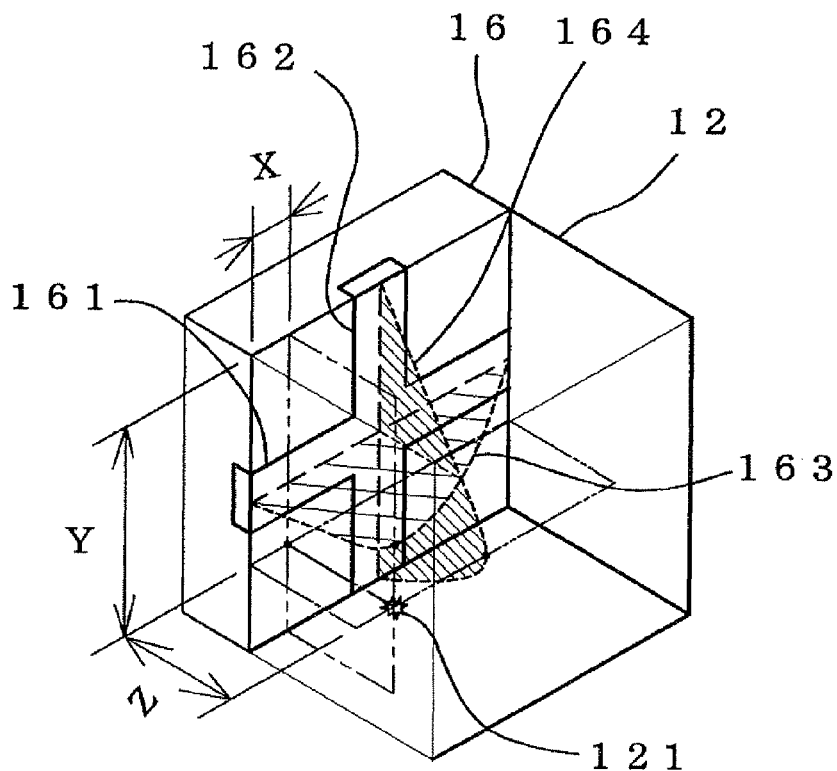
FIG. 3 is a perspective view of the same.

The photodetector 16 for the organic scintillator 12 can be configured such that a photo-detecting section of the photodetector optically faces part of a light extraction surface of the organic scintillator 12. A photodetector for obtaining a distribution of light generation in the X direction based on a fluorescence distribution analysis technique, and a photodetector for obtaining a distribution of light generation in the Y direction based on the fluorescence distribution analyzing technique, can be provided on the optically facing part. More specifically, as exemplified in FIG. 2 (plan view) and FIG. 3 (perspective view), a photo-detecting section 163 of the photodetector 16 can be arranged along the X and Y central axes of the light extraction surface of the organic scintillator 12. FIG. 3 shows how a photo-detecting section 161 extending in the X direction and a photo-detecting section 162 extending in the Y direction detect a position 121 at which fluorescent light is generated. The position 121 is defined above a position of the light extraction surface (in the Z direction) of the organic scintillator 12 that does not optically face the photo-detecting section of the photodetector 16. A photo-detecting section is shared at an intersection between the X and Y directions. As a matter of course, a photo-detecting section may be provided to cover the light extraction surface in its entirety. In FIG. 3, curves 163 and 164 show a distribution of the amount of light 121 at height Z detected by the photo-detecting section 161 in the X direction, and a distribution of the amount of light 121 at height Z detected by the photo-detecting section 162 in the Y direction, respectively.

Figure 4:
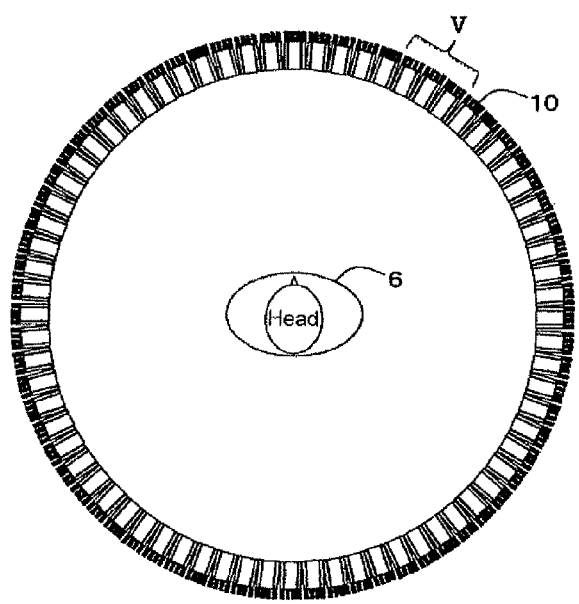
FIG. 4 is a cross sectional view showing the overall structure of a PET device utilizing the detector modules.
Figure 5:
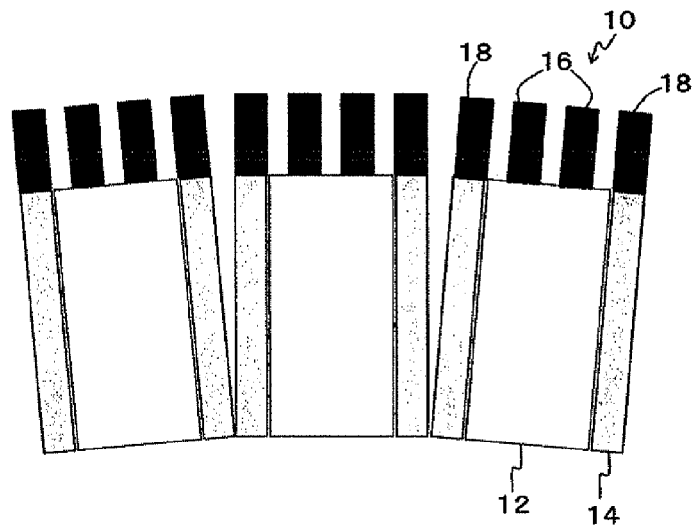
FIG. 5 is an enlarged cross sectional view of a section V of FIG. 4.
Figure 6:
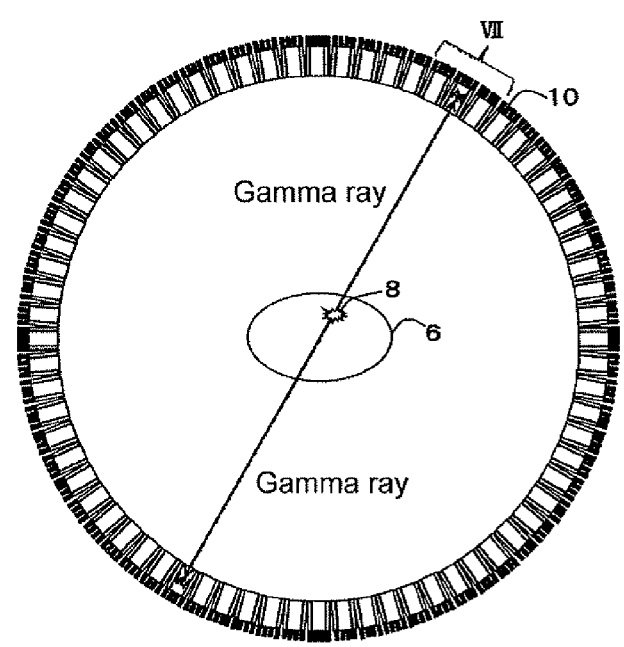
FIG. 6 is a sectional view showing simultaneous measurement of gamma rays in the PET device.
Figure 7:
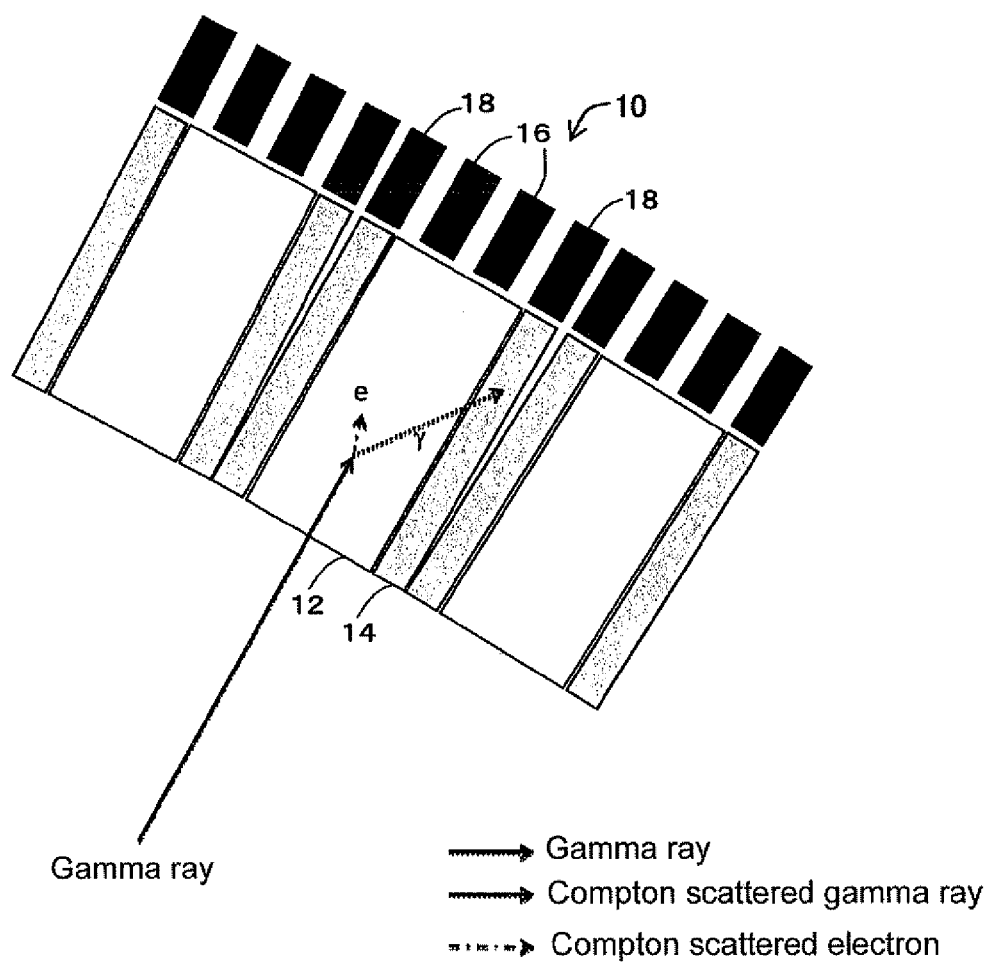
FIG. 7 is an enlarged cross sectional view of a section VII of FIG. 6.

As exemplified in FIG. 4 (general cross sectional view) and FIG. 5 (enlarged view of a section V of FIG. 4), a diagnostic device (such as a PET device) or a detector is formed by placing a large number of detector modules 10 to surround the target of measurement 6 (person or object). The PET device shown in FIG. 4 simultaneously measures two 511 keV gamma rays emitted from an internal body. Therefore, as shown in FIG. 6 (general view) and FIG. 7 (enlarged view of a section VII), two detector modules as a pair opposite each other are used, and each module detects one 511 keV gamma ray.

Figure 8:
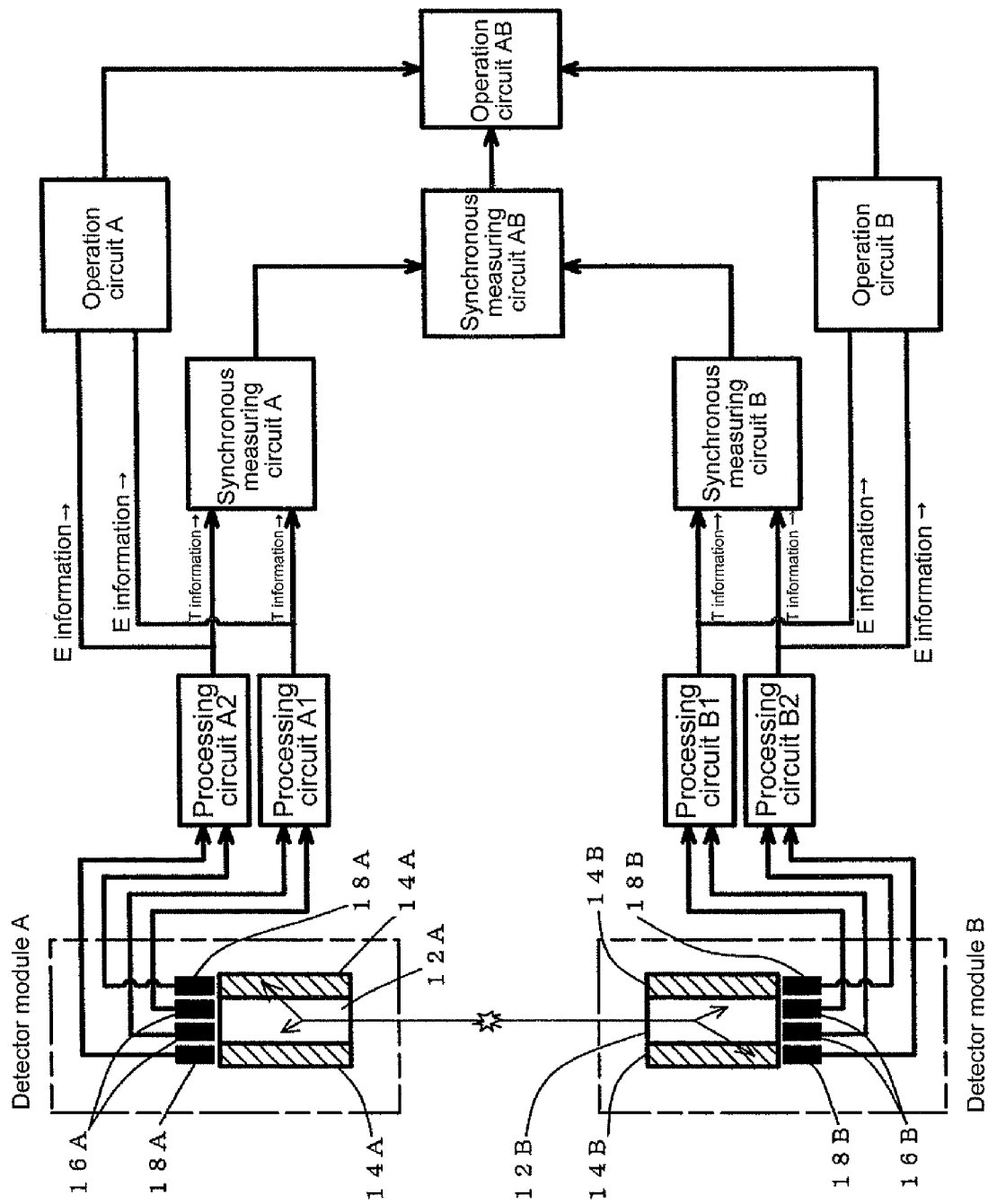
FIG. 8 is a block diagram for briefly explaining the invention.
Figure 9:
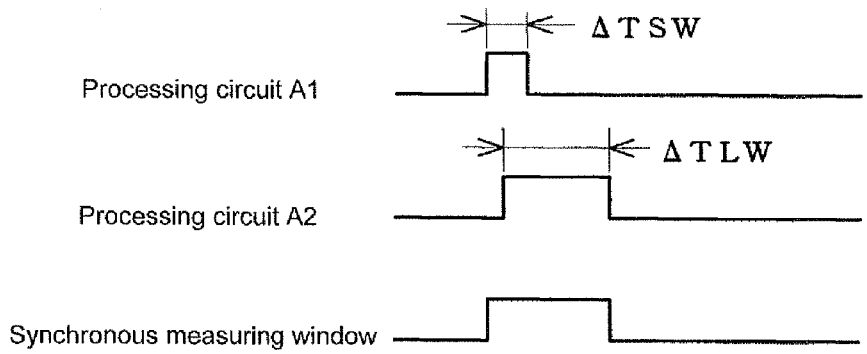
FIG. 9 is a time chart for briefly explaining the invention.
Figure 9:
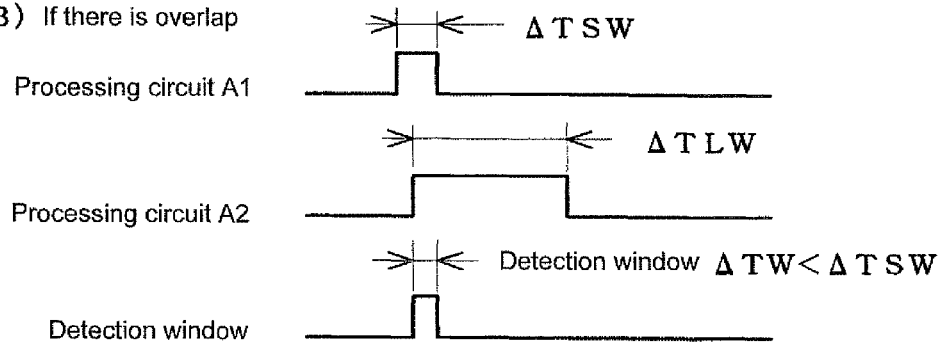
Figure 9:
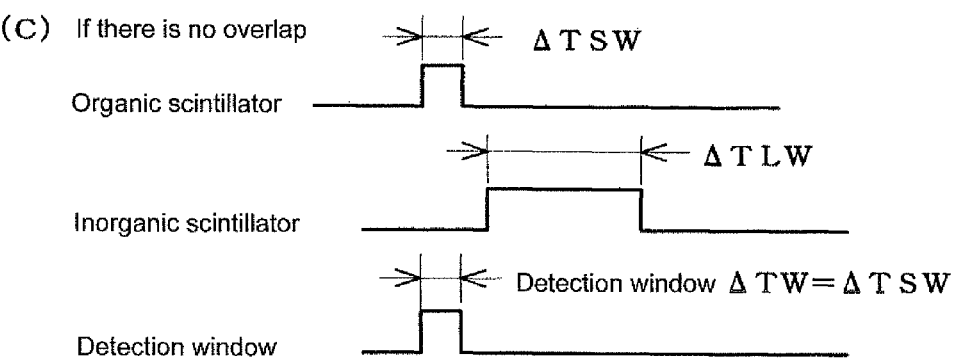

An analyzing method employed when the invention is applied to a PET device is briefly described first by using FIGS. 8 and 9. The analyzing method is thereafter described in detail by using the flow chart of FIG. 10.

In FIG. 8, a detector module A includes an organic scintillator 12A, two inorganic scintillators 14A, and photoelectric converters 16A and 18A for photoelectric conversion of light generation in the corresponding scintillator. In this example, two photoelectric converters 16A are optically coupled to the organic scintillator 12A, and the photoelectric converters 18A are each optically coupled to a corresponding one of the inorganic scintillators 14A. Light generated in a scintillator is photoelectrically converted, and is then given to a subsequent stage.

A processing circuit A1 performs A/D conversion of outputs from the photoelectric converters 16A in a former stage. A processing circuit A2 performs A/D conversion of outputs from the photoelectric converters 18A in a former stage. Resultant temporal information (T information) and energy information (E information) are separated, and then given to a subsequent stage.

The temporal information is obtained by detecting the rising edge of a signal given upon generation of light in each of the organic scintillator 12A and the inorganic scintillators 14A, and defining each rising edge as a time of light generation. Resultant information is given to a subsequent stage. As shown in FIG. 9(A), when receiving an input from the organic scintillator 12A, the processing circuit A1 generates a short-time window ΔTSW of a very short predetermined time width appropriate to the time width of corresponding light generation, and outputs the same to a subsequent stage. The processing circuit A2 generates a long-time window ΔTLW of a relatively long predetermined time width appropriate to the time width of light generation in the inorganic scintillator, and outputs the same to a subsequent stage. Energy information between these two types of time widths is also given to a subsequent stage.

Based on temporal information given from two circuits in a former stage including the processing circuits A2 and A1, a synchronous measuring circuit A checks to see if both times of light generation fall within a synchronous measuring window, thereby making a determination of synchronous measurement. More specifically, the synchronous measuring circuit A searches for a pair. The pair is such that a difference in time of outputs from the two processing circuits has been given to a synchronous measuring window of a predetermined time width. If such a pair is detected, the synchronous measuring circuit A determines that outputs from the pair are given on the basis of the same event, and makes a determination of synchronous measurement with the outputs from this pair. Then, the synchronous measuring circuit A calculates a time when an event was generated, namely a synchronous measuring time, on the basis of which the outputs from the pair was determined as synchronous measurement, and outputs the calculated synchronous measuring time to a subsequent stage.

The same process is performed for a detector module B.

Based on energy information given from two processing circuits including the processing circuits A2 and A1 in a former stage, and based on temporal information given from a simultaneous measuring circuit AB, an operation circuit A performs energy analysis, spatial analysis, and temporal analysis described later to determine the position of a radionuclide.

Each processing circuit, each synchronous measuring circuit, each operation circuit, the simultaneous measuring circuit AB, and the operation circuit AB are provided in the operation unit 20.

The analyzing method of the invention is described next by using the flow chart shown in FIG. 10. A detector module A (B) includes the organic scintillator 12A (B), the inorganic scintillators 14A (B), and the photoelectric converters 16A (B) and 18A shown in FIG. 8. When gamma rays emitted from a radionuclide enter the detector modules A and B (S0), lights are generated in the organic scintillator 12A (B) and the inorganic scintillators 14A (B). Next, the lights are converted by the photoelectric converters 16A (B) and 18A to an organic light generation signal (Sa1-1), an inorganic light generation signal (Sa1-2), an organic light generation signal (Sb1-1), and an inorganic light generation signal (Sb1-2). The light generation signals thereby generated are given to their post-stage processing circuits A1, A2, B1, and B2.

The processing circuits A1 (B1) and A2 (B2) are responsible for A/D conversion of input light generation signals. The processing circuit A1 (B1) generates a signal of a very short time width ΔTSW appropriate to the time width of light generation of the organic scintillator 12A (12B). The processing circuit A2 (B2) generates a signal of a time width ΔTLW appropriate to the time width of light generation of the inorganic scintillator 14A (14B). Temporal information (T information) obtained as a result of these A/D conversions is given to its corresponding post-stage synchronous measuring circuit A (B). Energy information (E information) obtained as a result of these A/D conversions is given to its corresponding post-stage operation circuit A (B). After the A/D conversions, each output signal is given an event ID (Sa2-3, Sb2-3). Therefore, signals can be related to each other in later statuses of the processing circuits A1, A2, B1, and B2.

Transition of temporal information having branched off from the processing circuits A1 (B1) and A2 (B2) is described here. Transition of energy information is described thereafter.

Transition of Temporal Information

The synchronous measuring circuit A (B) makes a determination of synchronous measurement by using outputs of the processing circuits A1 (B1) and A2 (B2). In this circuit, a synchronous measuring window of a predetermined time width is created first on the basis of the rising edge of a signal ΔTSW output from the processing circuit A1 (B1) as shown in FIG. 9(A). Next, the synchronous measuring circuit A (B)

makes a check to see if the rising edge of a signal ΔTLW output from the processing circuit A2 (B2) falls within the created synchronous measuring window. If the rising edge of the signal ΔTLW falls within the synchronous measuring window, the synchronous measuring circuit A (B) makes a determination of synchronous measurement. A detection window ΔTW as a synchronously measured flag is given as a result of the measurement to a subsequent stage. Temporal information about the signals ΔTSW and ΔTLW having reached the synchronous measuring circuit A (B) are also given to the subsequent stage.

Next, it is described how the performance of simultaneous measurement used in a PET device and the like is enhanced by using the detection window ΔTW created by the simultaneous measuring circuit A (B) when a determination of simultaneous measurement is made. As described above, in simultaneous measurement, a narrower detection window reduces noise events, thereby enhancing detection efficiency.

A conventional PET device such as the one disclosed in a publication (Japanese Patent Application Laid-Open No. 2007-71858 A (Shimadzu Cooperation), Mar. 22, 2007) uses an inorganic scintillator. Accordingly, in this case, the signal ΔTLW is applied as the detection window ΔTW. In contrast, use of the detector module of the invention with the organic scintillator 12A (12B) and the inorganic scintillators 14A (14B) eliminates the need to apply the signal ΔTLW of a long time width as the detection window ΔTW by employing a synchronous measuring technique.

As shown in FIG. 9(B), the signals ΔTSW and ΔTLW generally overlap each other. In synchronous measurement, an overlapping time width is set to the detection window ΔTW. If the signals ΔTSW and ΔTLW do not overlap each other as shown in FIG. 9(C), the signal ΔTSW of a shorter time width may be set as the detection window ΔTW.

In the case of a detector with only an organic scintillator, the signal ΔTSW is applied as a detection window. Accordingly, the detection window is short in terms only of temporal information. However, this detector is not suitably applied for detecting a gamma ray for the reason mentioned above. In contrast, use of the detector module of the invention with the organic scintillator 12A (12B) and the inorganic scintillators 14A (14B) realizes the detection window ΔTW shorter than the signal ΔTSW as shown in FIG. 9(B), while realizing effective detection of a gamma ray.

The simultaneous measuring circuit AB performs simultaneous measurement by using output signals from the synchronous measuring circuits A and B. ΔTWs set in FIGS. 9(B) and 9(C) used in this simultaneous measurement are both smaller by several digits than ΔTW that is set in a conventional PET device such as the one disclosed in a publication (Japanese Patent Application Laid-Open No. 2007-71858 A (Shimadzu Cooperation), Mar. 22, 2007). Accordingly, application of the invention to a PET device and the like enhances measurement accuracy in simultaneous measurement, effectively removes an accidental background event, and enhances the performance of the device. This constitutes one of the distinguishing features of the invention.

The simultaneous measuring circuit AB calculates a measuring time based on detection windows output from the synchronous measuring circuits A and B. If these detection windows are defined according to the same standard, a measurement time is accurately calculated. More specifically, the standard may be the rising edge and the center of a detection window, and others.

Transition of Energy Information

Figure 11:
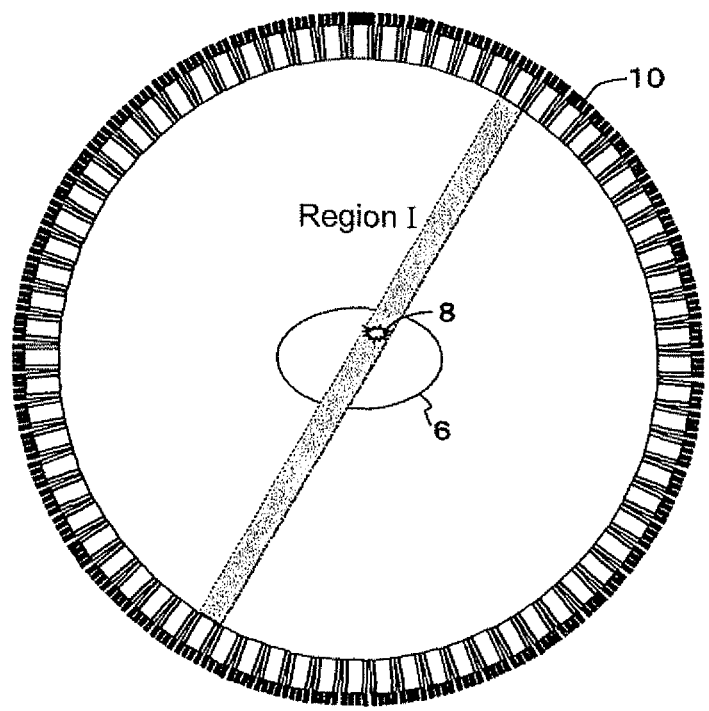
FIG. 11 is a sectional view for briefly explaining energy analysis.

Transition of energy information having branched off from the processing circuits A1 (B1) and A2 (B2) is described below. The operation circuit A (B) adds energy in the interval of the signal ΔTSW output from the processing circuit A1 (B1), and energy in the interval of the signal ΔTLW output from the processing circuit A2 (B2). The operation circuit A (B) performs energy analysis using this addition, thereby reconstructing the energy of the gamma rays having entered the detector module (S0). As a result, the position of the radionuclide 8 is limited to that in a belt-shaped region I as shown in FIG. 11.

More specifically, when energy information about the time width of the short-time window ΔTSW is received from the processing circuit A1, received energy is added up (Sa8). When energy information about the time width of the long-time window ΔTLW is received from the processing circuit A2, the received energy is added up (Sa9). Then, by referring to an ID number given in status (Sa2-3), only data for which a determination of synchronous measurement is made in status 4 is selected, and two energy is added, thereby obtaining total energy (Sa10). Next, based on the total energy information thereby obtained, a position of light generation (position P) in a scintillator is calculated (Sa11) by using a spatial analysis technique described later.

Next, association with simultaneous measuring information is still established in status (S14), thereby creating a list including a time of light generation (T), energy (E), and a position of light generation (P) in order of an event ID number of simultaneous measurement (S14).

In this energy analysis technique, a signal resulting from Compton scattering that has been regarded as a noise is treated as a true signal. Accordingly, influence of a noise resulting from Compton scattering is not required to be considered in an energy region of a gamma ray to be measured.

Next, spatial analysis is performed in status (S15) to obtain the coordinates of an interaction point of a gamma ray in each of the organic scintillators 12A and 12B by using a scintillation distribution obtained by the photodetector 16 connected to the organic scintillator 12.

A technique of obtaining the coordinates of an interaction point of a gamma ray during spatial analysis used in status (S15) is described in detail below.

Figure 12:
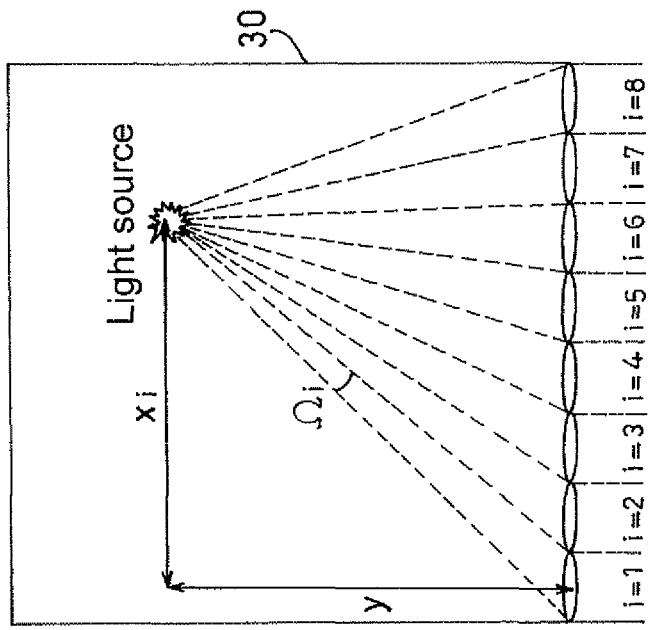
FIG. 12(A) shows light propagation.
FIG. 12(B) shows a solid angle from a light source in a method of obtaining interactive coordinates by using a scintillation distribution.
Figure 12:
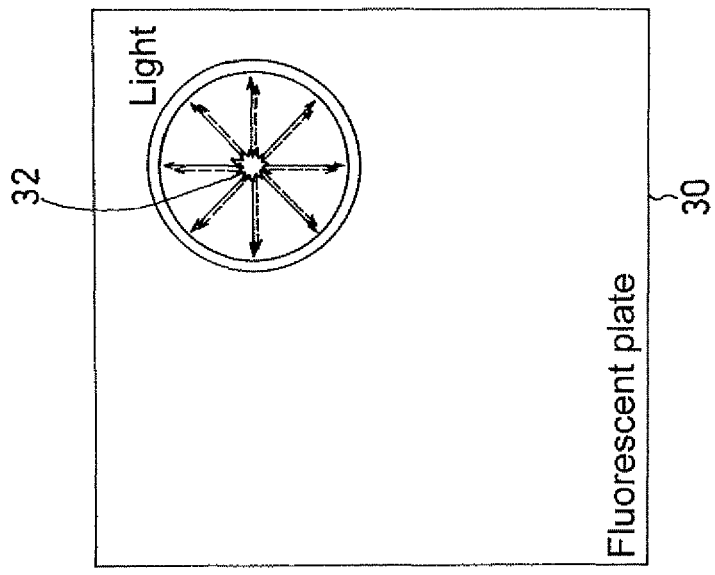

The centroid technique has conventionally been employed to determine a light source 32 of a fluorescent plate 30 shown in FIG. 12. According to the centroid technique, a center of gravity is obtained from a ratio of light amounts between photodetectors (photomultiplier tubes, for example) placed on the right and left sides of the fluorescent plate 30, thereby calculating a position. However, this technique only makes it possible to determine the "relative position" of a light source (to determine which one of the right and left photodetectors generates fluorescent light). Unlike this conventional way, a fluorescence distribution analysis technique described next is a new analysis technique of directly obtaining the absolute position of a light source. This technique offers performance by using an organic scintillator (such as a plastic scintillator and a p-terphenyl) composed of molecules of a small mass number such as carbon and hydrogen. Light generated in the fluorescent plate 30 is uniformly emitted in all directions as shown in FIG. 12(A). Then, as shown in FIG. 12(B), the emitted light reaches a side surface after repeating total reflection at a front surface of the fluorescent plate 30. Light is absorbed very little in an organic scintillator during its propagation as a result of a small mass number of the organic scintillator. Thus, a distribution of the amount of light obtained at the side surface can be described as the solid angle of light when it is emitted. (This technique is applicable to an inorganic scintillator of a large mass number. However, this case requires calculation in consideration of an element of influence of light absorption during light propagation, or influence of density distribution in a fluorescent plate. Accordingly, calculation cannot be made only with a solid angle.)

Here, in order to obtain a distribution of the amount of light, a plurality of photodetectors (such as photomultiplier tubes, multianode photomultiplier tubes with a plurality of cells, and semiconductor photodetectors) are arranged in a line on the side surface as shown in FIG. 12(B).

The solid angle $\Omega_i$ of a photodetector as viewed from a light source, which has an area with a radius r and which is placed at some side surface (here, photodetectors i include first to eighth photodetectors spaced a distance d), is expressed by the following formula:

$$\Omega_i = (\pi r^2 \times y)/(x_i^2 + y^2)^{3/2} \quad (8)$$

Here, i represents the number of a photodetector, $x_i$ represents a distance along the x axis between the light source and an $i^{th}$ photodetector, and y represents a distance between the light source and a side surface on which a photodetector is placed.

What is important here is that y is constant in obtaining solid angles of photodetectors placed on the same surface, irrespective of the location (i=1 to 8) of the photodetectors. Further, $x_i$ is expressed by the following formula by using the distance $x_1$ between the light source and a photodetector (i=1), and the distance d between photodetectors:

$$x_i = x_1 - d \times (i-1) \quad (9)$$

In the case of an organic scintillator of a small mass number, the amount of light Pi measured by a photodetector (i) is described by a solid angle as expressed as follows:

$$P_i \propto \Omega_i = A \times \Omega_i \quad (10)$$

Here, A is a constant of proportionality.

A distribution of the amount of light obtained at the side surface is expressed by three variables (A, $x_i$, y) by combining formulas (8), (9) and (10) together.

$$Pi = A \times (\pi r^2 \times y)/(\{x_i - d \times (i-1)\}^2 + y^2)^{3/2} \quad (11)$$

The absolute position ($x_1$, y) of fluorescent light can be obtained by fitting formula (11) to a distribution of the amount of light Pi that is actually obtained at a photodetector (i=1 to 8).

Figure 13:
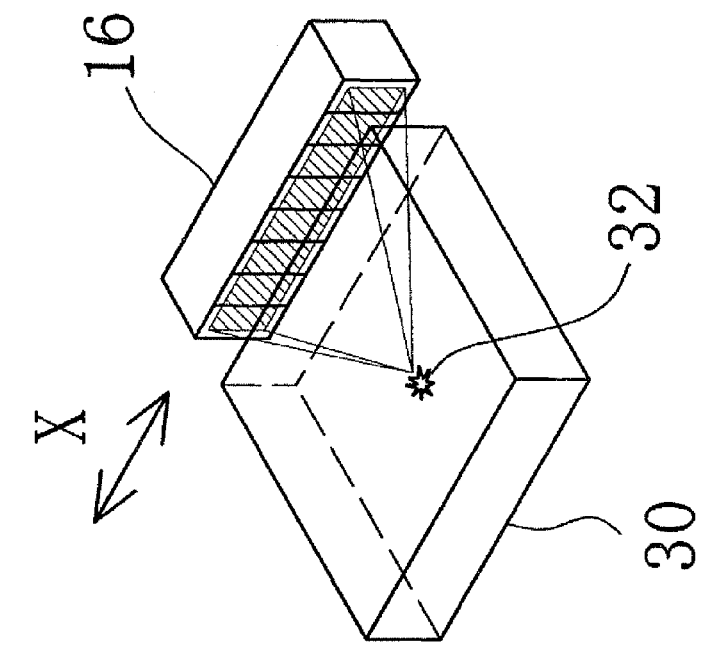
FIG. 13(A) shows calculation of two-dimensional coordinates.
FIG. 13(B) shows calculation of three-dimensional coordinates for explaining a fluorescence distribution analysis technique in spatial analysis.
Figure 13:
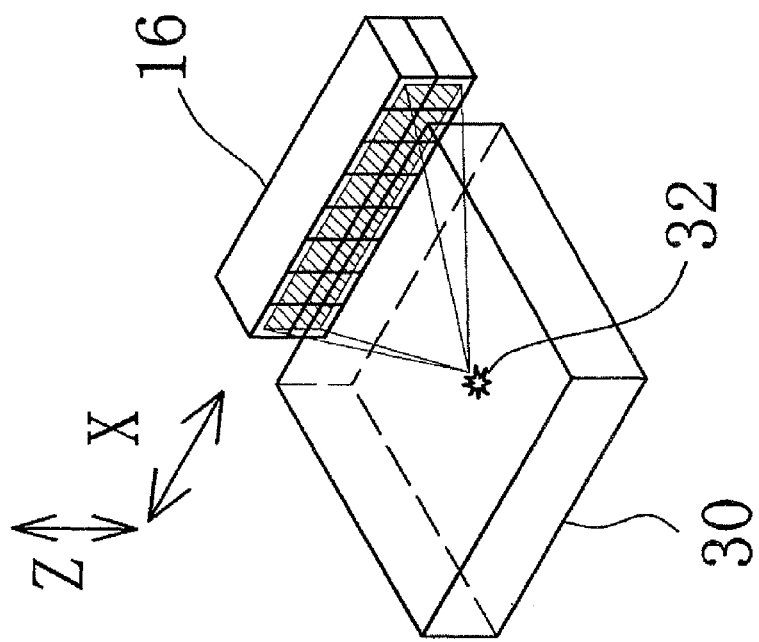

Two-dimensional coordinates (X direction) can be calculated as shown in FIG. 13(A) by using this technique. Information in the Z direction is also obtained if a fluorescent plate is viewed from a group of photodetectors arranged in several layers (in the figure, two layers in a direction of height) that are optically opposite the fluorescent plate.

Figure 14:
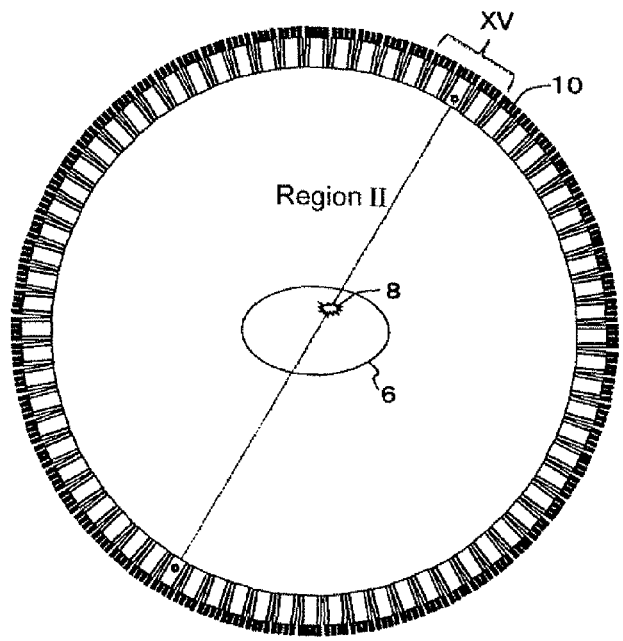
FIG. 14 is a cross sectional view for briefly explaining temporal analysis.
Figure 15:
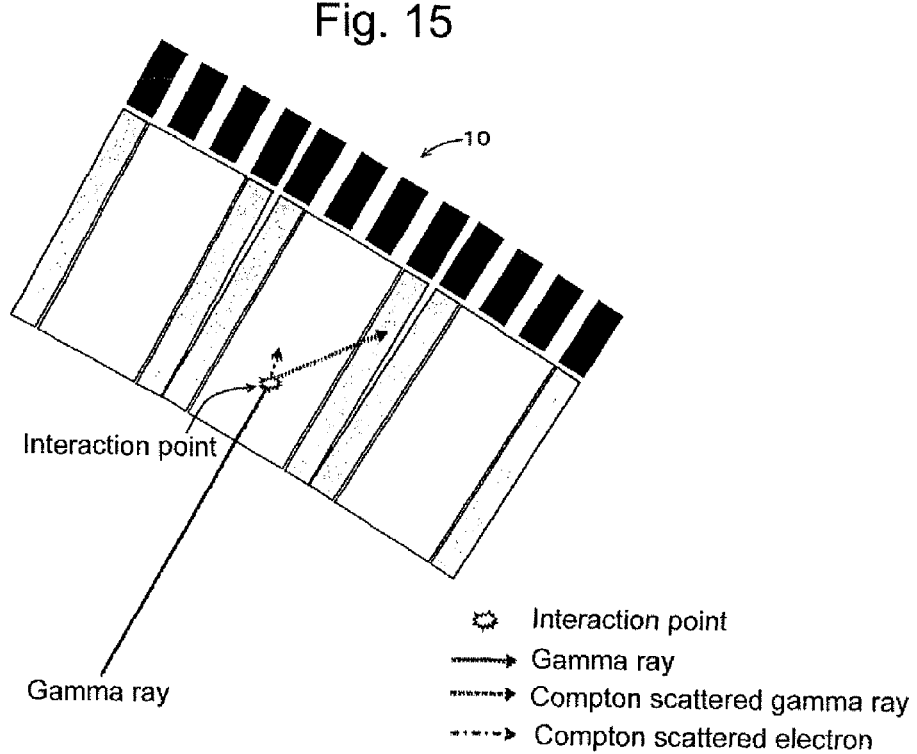
FIG. 15 is an enlarged cross sectional view of a section XV of FIG. 14.

Then, the coordinates of an interaction point in two symmetrically arranged organic scintillators are connected by a line. As a result, the belt-shaped region I shown in FIG. 11 specified only by energy information can be specified to the line of a linear region II shown in FIG. 14 (general view) and FIG. 15 (enlarged view of a section XV).

In contrast, in the conventional technique, this line is obtained by Fourier analysis. This means that analysis takes a long time, so that a result of diagnosis does not come out on the day of testing in many cases. According to the present invention, a line is obtained even during measurement without any difficult analysis. Thus, a time for analysis is considerably reduced, and a result of diagnosis comes out on the same day, thereby easing examinee's anxiety.

Further, as the emission angle of a gamma ray is known, there is no need to provide a collimator required in conventional PET systems. Thus, a PET system is allowed to be considerably reduced in weight.

Figure 16:
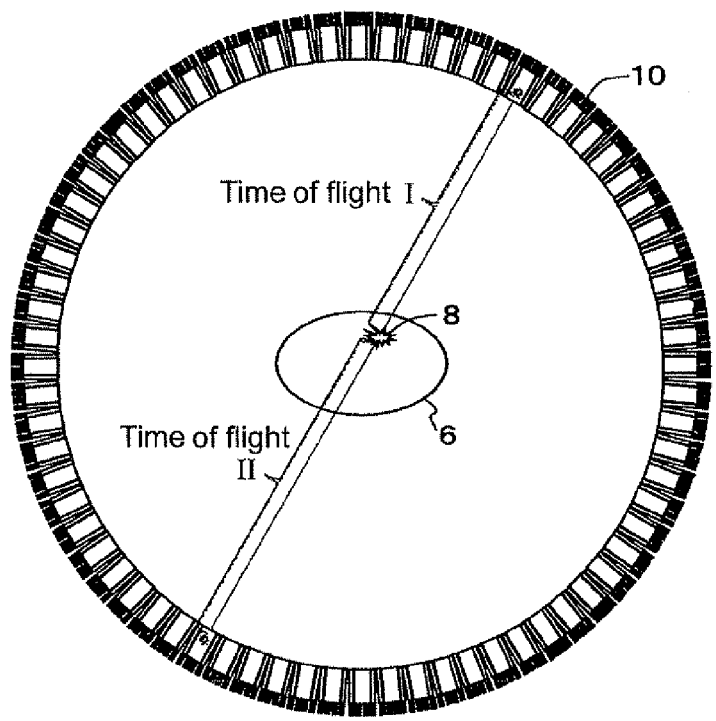
FIG. 16 is a cross sectional view for briefly explaining spatial analysis.

Next, temporal analysis is performed on the basis of TOF principles in status (S16). Then, a flight distance is narrowed down by using a difference between arrival times (times of flight) I and II of gamma rays at two opposite organic scintillators as shown in FIG. 16. Thus, the position of the radionuclide 8 is specified in the linear region II obtained from energy and spatial information (S17). A program shown in FIG. 10 can be stored in a computer-readable recording medium such as a hard disk and a ROM.

The region I may also be specified to the line of the region II in the following way. In this way, the processes in statuses (Sa11) and (Sa12) shown in FIG. 10 are replaced by analysis by using Fourier conversion as in the conventional technique.

Or, after the limitation to the region I, a distance from an organic scintillator to a target of measurement may be obtained by using a TOF analysis technique.

Conventionally used PET devices try to conduct TOF with an inorganic scintillator of slow time response. In contrast, introducing an organic scintillator of fast time response allows TOF to be put to practical use in PET devices. A rate of removal of an accidentally generated noise signal is proportional to the time width of the foregoing detection window. A noise signal is removed for the considerably reduced time width of the detection window ΔT, compared to that of a conventionally used inorganic scintillator. That is, measurement at a high S/N ratio is realized.

Figure 17:
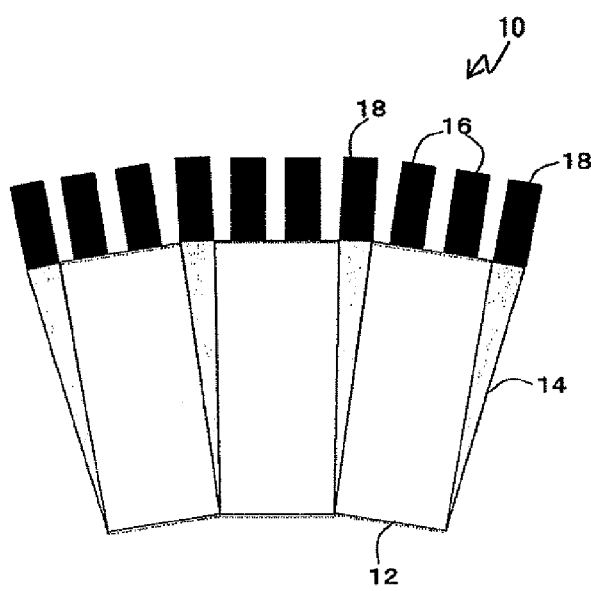
FIG. 17 is a cross sectional view showing a second embodiment of a detector module according to the present invention.

A module of a rectangular parallelepiped is used in the foregoing embodiment. In a second embodiment shown in FIG. 17, the inorganic scintillators 14 of a wedge shape may be arranged in a circle as shown in FIG. 4. In this case, the sharp ends of the wedges point to a target of measurement. The present embodiment allows a module to be effectively arranged in a PET device and the like. Further, the organic scintillators 12 may have a trapezoidal shape.

Figure 18:
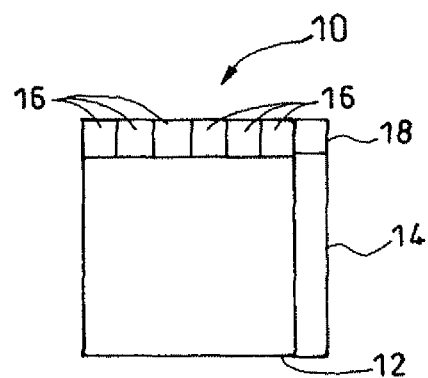
FIG. 18 is a cross sectional view showing a third embodiment of the same.
Figure 19:
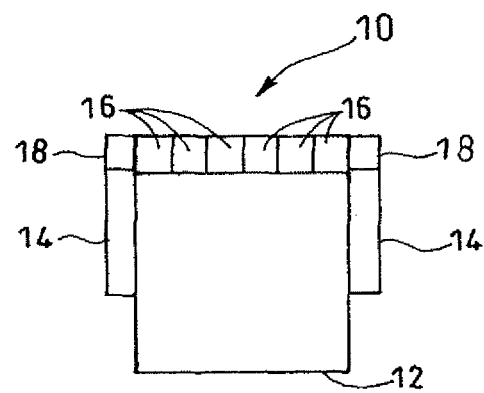
FIG. 19 is a cross sectional view showing a fourth embodiment of the same.
Figure 20:
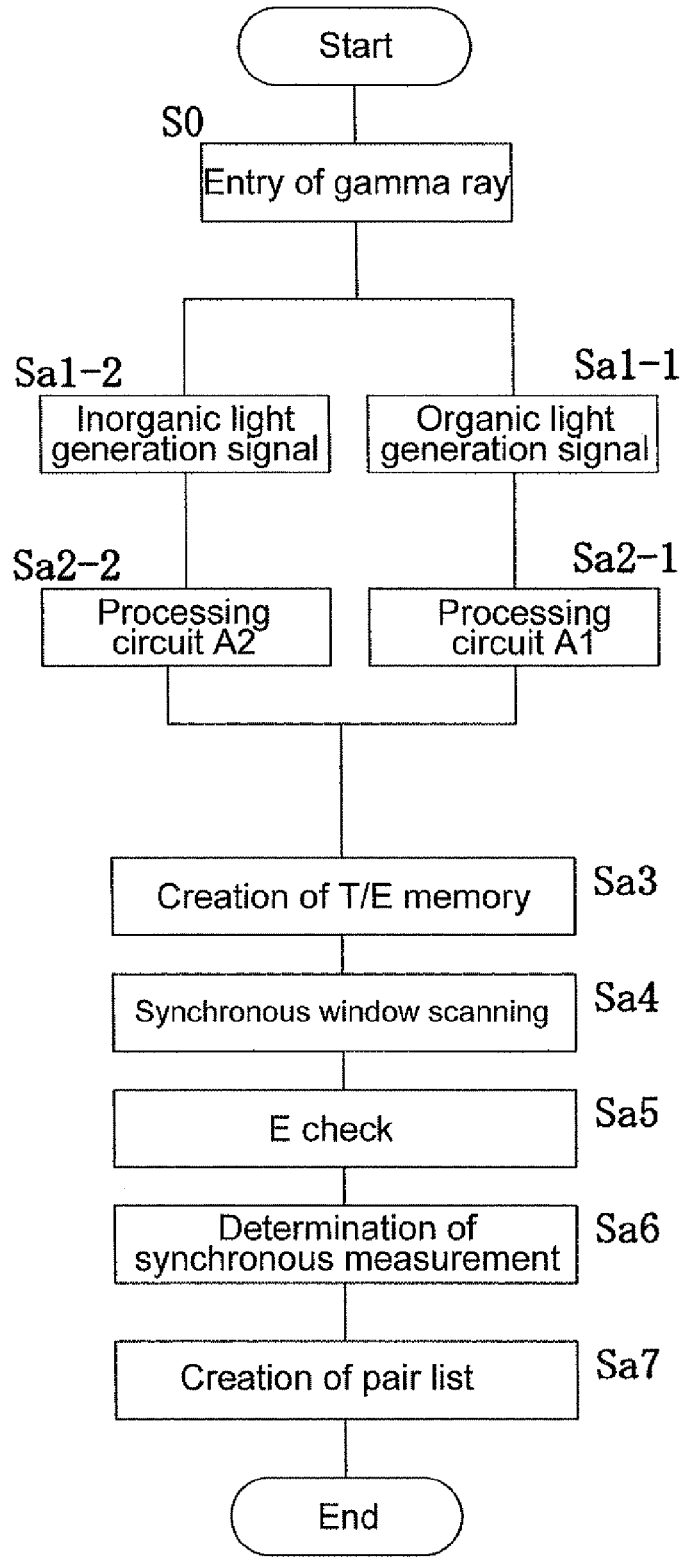
FIG. 20 is a flow chart for briefly explaining a synchronous measuring technique.
Figure 21:
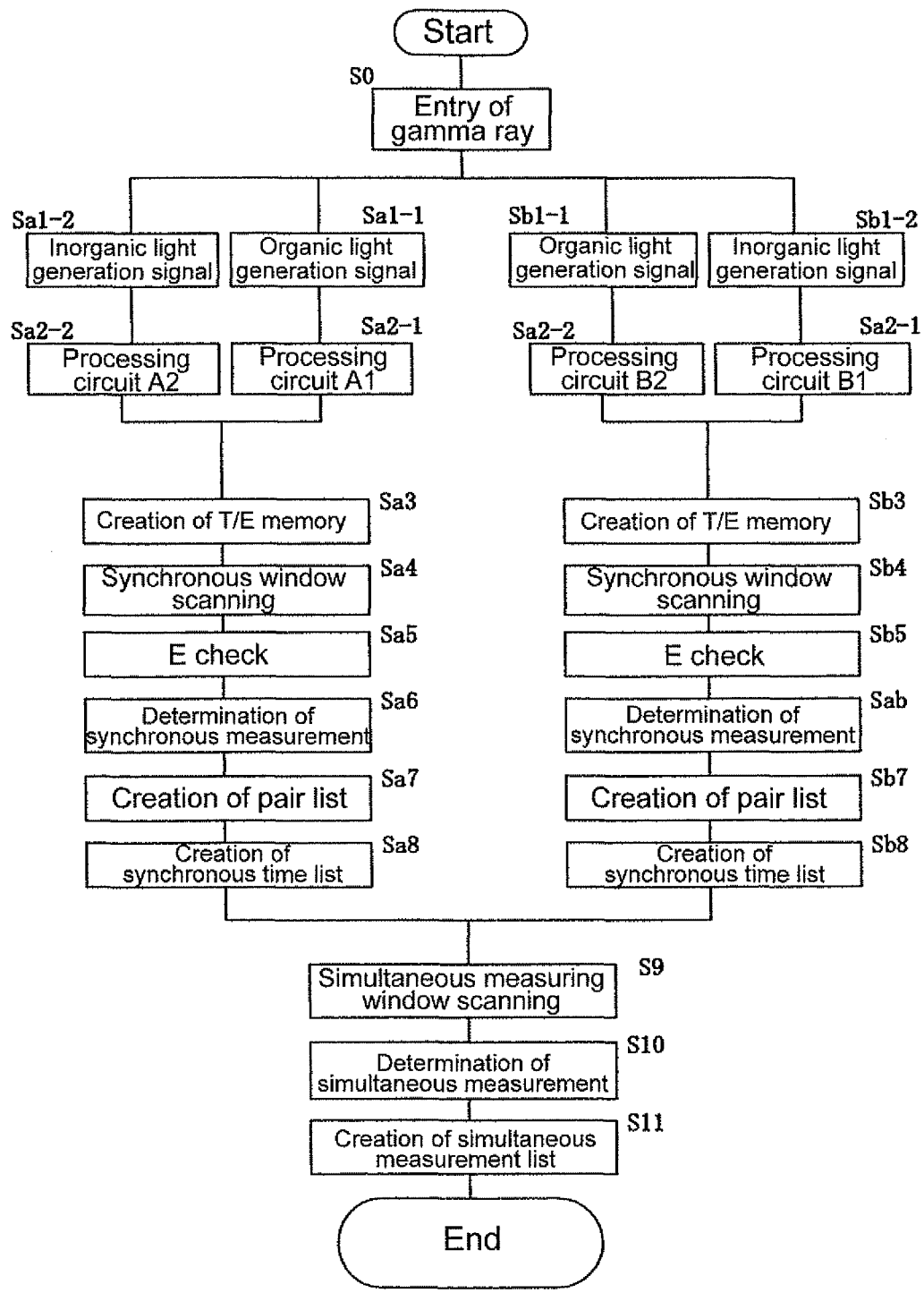
FIG. 21 is a flow chart for explaining an application of the synchronous measuring technique.
Figure 23:
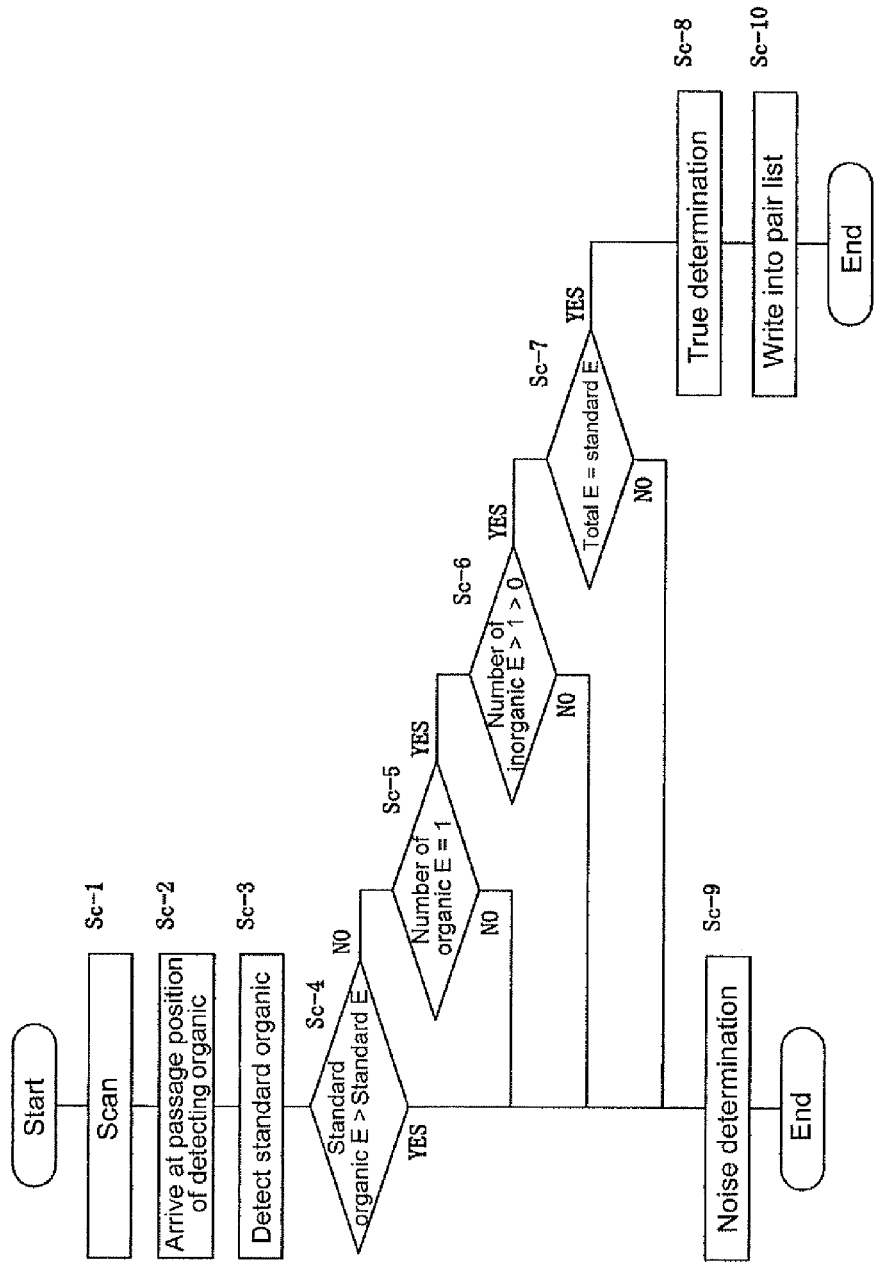
FIG. 23 is a simple example of the synchronous measuring technique.

In both of the embodiments described above, the inorganic scintillators 14 are arranged on opposite sides of the organic scintillator 12. However, as in a third embodiment shown in FIG. 18, the inorganic scintillator 14 may be placed only on one side of the organic scintillator 12. Further, as in a fourth embodiment shown in FIG. 19, the inorganic scintillators 14 may be disposed to extend halfway along the organic scintillator 12.

Figure 10:
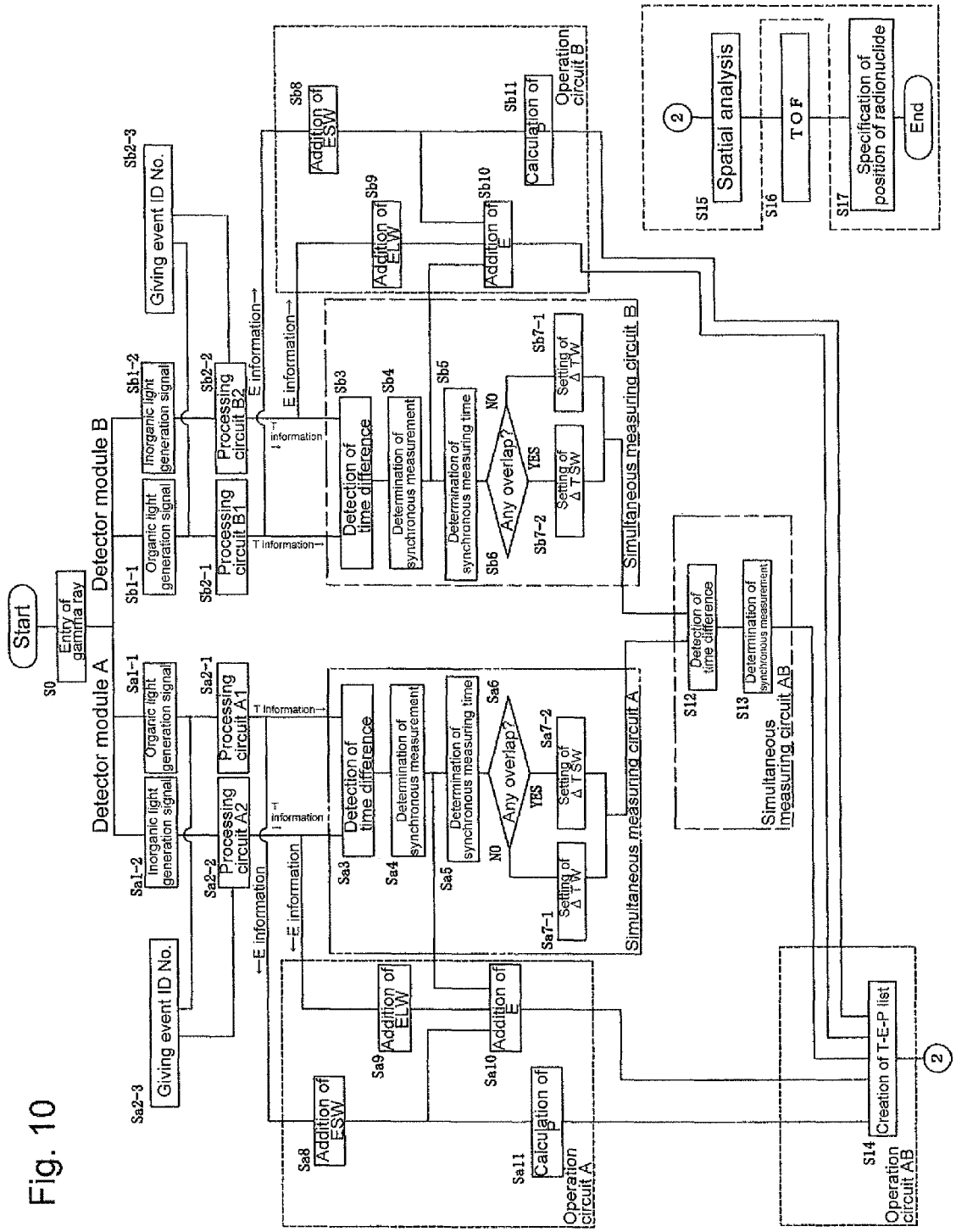
FIG. 10 is a flow diagram for briefly explaining the invention.

The PET device shown in FIG. 10 is used as an example in the foregoing description. However, the applicability of the invention is not limited to the PET device. The invention is also applicable to an SPECT device part of which is surrounded by dashed lines in FIG. 10, other tomography devices, other radiation diagnostic devices, and the like.

In order to introduce more scintillation light into a photodetector, each of the organic and inorganic scintillators 12 and 14 may be covered with a reflector.

Industrial Applicability

A gamma ray detector capable of realizing super-sensitivity at low cost without using a collimator, a radiation diagnostic device using the gamma ray detector, a tomography device such as a PET and an SPECT, and a method of analyzing the tomography device can be realized.

The invention claimed is:

1. A gamma ray detector for detecting a gamma ray emitted from a target of measurement, comprising:
    an organic scintillator for detecting Compton electrons resulting from a gamma ray emitted from the target of measurement;
    an inorganic scintillator for detecting a Compton gamma ray; and
    photodetectors for detecting light generation in the corresponding scintillators, wherein the gamma ray detector performs synchronous measurement to select a pair according to a same event by using a time and energy detected by each of the photodetectors on the basis of light generation in the organic scintillator and the inorganic scintillator, and an interval of a detection window to be generated is changed between when a very short short-time window appropriate to a time width of light generation in the organic scintillator and a relatively long long-time window appropriate to a time width of light generation in the inorganic scintillator overlap each other, and when they do not overlap each other, so as to enhance measurement accuracy.

2. The gamma ray detector according to claim 1, wherein if the detector modules are provided as a pair, the detector modules each perform synchronous measurement, thereby enhancing performance of noise removal.

3. The gamma ray detector according to claim 2, wherein a detection window of a gamma ray when a determination of synchronous measurement is made is employed as a standard of a detected time of light generation in the organic scintillator.

4. The gamma ray detector according to claim 1, wherein if the very short short-time window appropriate to the time width of light generation in the organic scintillator and the relatively long long-time window appropriate to the time width of light generation in the inorganic scintillator overlap each other, an overlapping interval is defined as a detection window, and is employed as a standard of a detected time.

5. The gamma ray detector according to claim 1, wherein if the very short short-time window appropriate to the time width of light generation in the organic scintillator and the relatively long long-time window appropriate to the time width of light generation in the inorganic scintillator do not overlap each other, the very short short-time window appropriate to the time width of light generation in the organic scintillator is defined as a detection window, and is employed as a standard of a detected time.

6. The gamma ray detector according to claim 1, wherein an accuracy of a time measured in simultaneous measurement is enhanced by measuring the time on the basis of the synchronous measuring window.

7. The gamma ray detector according to claim 1, wherein gamma rays emitted from the target of measurement are reconstructed by adding absorbed amounts of energy of the gamma rays synchronously measured in the two types of scintillators.

8. The gamma ray detector according to claim 1, wherein a region of emission from the target of measurement is limited by arranging the detector modules as a pair to place the target of measurement therebetween, and by making each of the detector modules reconstruct a gamma ray.

9. A gamma ray detector, wherein the region of emission limited in claim 8 is specified to a line by a position of emission from the target of measurement is specified to that on the line without performing Fourier conversion by arranging the detector modules as a pair to place the target of measurement therebetween, and by connecting positions by the line where gamma rays are generated in the corresponding organic scintillators.

10. The gamma ray detector according to claim 9, wherein a time of flight is analyzed by using respective outputs from the detector modules as a pair.

11. A gamma ray detector, wherein a distance from the organic scintillator to the target of measurement is determined in the region of emission limited in claim 8 by analyzing a time of flight.

12. The gamma ray detector according to claim 1, wherein a position of emission from the target of measurement is specified to that on a line without performing Fourier conversion by arranging the detector modules as a pair to place the target of measurement therebetween, and by connecting positions by the line where gamma rays are generated in the corresponding organic scintillators.

13. The gamma ray detector according to claim 1, wherein the inorganic scintillator is arranged on a side surface of the organic scintillator.

14. The gamma ray detector according to claim 13, wherein the inorganic scintillator has a wedge shape with a sharp edge pointing to the target of measurement.

15. The gamma ray detector according to claim 1, wherein the photodetector is arranged such that a photo-detecting section of the photodetector optically faces part of a light extraction surface of the scintillator, and wherein a photodetector for obtaining a distribution of light generation in an X direction based on a fluorescence distribution analysis technique, and a photodetector for obtaining a distribution of light generation in a Y direction based on the fluorescence distribution analyzing technique, are provided on the optically facing part.

16. The gamma ray detector according to claim 15, wherein the photodetectors are arranged along X and Y central axes of the light extraction surface of the scintillator.

17. The gamma ray detector according to claim 1, wherein data obtained by simultaneous measurement of a synchronously measured event is constructed into an image without performing Fourier conversion, so as to reduce time for image formation and enhance image accuracy.

18. The gamma ray detector according to claim 1, wherein the gamma ray detector is employed as a single detector module.

19. The gamma ray detector according to claim 18, wherein the gamma ray detector is employed as a detector for an SPECT device.

20. The gamma ray detector according to claim 1, wherein the gamma ray detector is employed as a detector for a PET device.

21. A radiation diagnostic device comprising the gamma ray detector according to claim 1, the gamma ray detector arranged around a target of measurement.

22. A tomography device comprising the gamma ray detectors according to claim 1, the gamma ray detectors arranged as a pair in order to detect annihilation gamma rays as a pair emitted in opposite directions from a target of measurement.

23. The tomography device according to claim 22, for analyzing times of flight by using outputs from the gamma ray detectors as a pair.

24. A method of analyzing a tomography device, the method being performed on the tomography device according to claim 22, the method comprising:

a step of identifying energy in a detection window of a gamma ray suitable for characteristics of the organic scintillator;

a step of identifying a gamma ray by using a sum of energy of the organic scintillator and the inorganic scintillator;

a step of calculating fluorescent coordinates in the organic scintillator by using a scintillation distribution of the organic scintillator;

a step of specifying a region specified only by energy information to a line by connecting fluorescent coordinates in the two organic scintillators as a pair by a line; and a step of specifying three-dimensional coordinates of a radionuclide on the line by using a difference between arrival times of gamma rays at the two organic scintillators as a pair.

25. A computer program readable from a recording medium, for causing a computer to execute the method of analyzing a topography device according to claim 24.

26. A computer-readable recording medium that stores the computer program according to claim 25.

27. A gamma ray detector for detecting a gamma ray emitted from a target of measurement, comprising:
- an organic scintillator for detecting Compton electrons resulting from a gamma ray emitted from the target of measurement:
- an inorganic scintillator for detecting a Compton gamma ray; and
- photodetectors for detecting light generation in the corresponding scintillators, wherein
- a time and energy detected by the photodetector for the inorganic scintillator, and those detected by the photodetector for the organic scintillator are scanned along a time axis within a synchronous scanning window of a predetermined time interval, and wherein a flag in the synchronous scanning window is detected immediately before the synchronous scanning window passes through an organic flag.

28. The gamma ray detector according to claim 27, wherein a sum of detected energy of all flags in the synchronous scanning window is obtained immediately before the synchronous scanning window passes through the organic flag, and wherein if the sum is smaller than a reference level of emitted energy of a gamma ray, the organic flag is determined as a noise.

29. The gamma ray detector according to claim 27, wherein the energy of the organic flag is detected immediately before the synchronous scanning window passes through the organic flag, and wherein if the detected energy is greater than a reference level of emitted energy of a gamma ray, the organic flag is determined as a noise.

* * * * *